United States Patent
Arnin

(10) Patent No.: US 9,622,786 B2
(45) Date of Patent: Apr. 18, 2017

(54) SPINAL CAGE

(71) Applicants: APIFIX LTD., Misgav (IL); David Klein, Rehovot (IL)

(72) Inventor: Uri Arnin, Kiryat Tivon (IL)

(73) Assignee: Apifix Ltd., Carmiel (IL)

( * ) Notice: Subject to any disclaimer, the term of this patent is extended or adjusted under 35 U.S.C. 154(b) by 301 days.

(21) Appl. No.: 14/370,964

(22) PCT Filed: Jan. 7, 2013

(86) PCT No.: PCT/US2013/020454
§ 371 (c)(1),
(2) Date: Jul. 8, 2014

(87) PCT Pub. No.: WO2013/106263
PCT Pub. Date: Jul. 18, 2013

(65) Prior Publication Data
US 2014/0330387 A1    Nov. 6, 2014

Related U.S. Application Data

(60) Provisional application No. 61/631,667, filed on Jan. 9, 2012, provisional application No. 61/690,835, filed on Jul. 6, 2012, provisional application No. 61/743,418, filed on Sep. 4, 2012.

(51) Int. Cl.
*A61F 2/44* (2006.01)
*A61B 17/70* (2006.01)

(52) U.S. Cl.
CPC ...... *A61B 17/7014* (2013.01); *A61B 17/7001* (2013.01); *A61B 17/7076* (2013.01); *A61F 2/4425* (2013.01); *A61F 2/4455* (2013.01)

(58) Field of Classification Search
None
See application file for complete search history.

(56) References Cited

U.S. PATENT DOCUMENTS

| | | | |
|---|---|---|---|
| 5,609,635 A | 3/1997 | Michelson | |
| 6,685,742 B1 * | 2/2004 | Jackson | A61F 2/447 623/17.11 |
| 2005/0234555 A1 | 10/2005 | Sutton | |

FOREIGN PATENT DOCUMENTS

WO    2006/065419    6/2006

OTHER PUBLICATIONS

PCT Written Opinion and Search PCT/US2013/020454, Aug. 16, 2013.

* cited by examiner

*Primary Examiner* — Sameh Boles
(74) *Attorney, Agent, or Firm* — Dekel Patent Ltd.; David Klein

(57) ABSTRACT

A spinal cage (80) including first and second spinal attachment members (82, 84) attachable to vertebrae (83, 85), the first and second spinal attachment members (82, 84) articulating with one another by means of an articulation joint (86, 88), characterized by a wedge element (90) arranged for wedging between the first and second spinal attachment members (82, 84), and an actuator (92) linked to the wedge element (90) for moving the wedge element (90) in a direction that wedges the wedge element (90) further in between the first and second spinal attachment members (82, 84) or further away from the first and second spinal attachment members (82, 84).

7 Claims, 3 Drawing Sheets

SPINAL CAGE

FIELD OF THE INVENTION

The present invention relates generally to spinal implants and prostheses, and particularly to a rotatable spinal cage.

BACKGROUND OF THE INVENTION

Scoliosis is a spinal deformity affecting many people. Current surgical treatment involves affixing long fusion rods to the spine by pedicle screws. The rod system is intended to force the deformed spine into a more healthy position. Other spinal disorders which are often treated by fusion include hyperkyphosis and hyperlordosis.

SUMMARY OF THE INVENTION

The present invention also seeks to provide an improved way to correct spinal deformity by using a spinal cage inserted between adjacent vertebral bodies. The spinal cage is built in a way that it has a rotational pivot and a mechanism to allow rotation in one direction while preventing rotation in the opposite direction.

In one embodiment of the present invention, the spinal cage is rotated (pivoted) by a wedge that can slide or move towards the cage's center of rotation along an inclined surface. The wedge can move by being pulled or pushed by an actuator (e.g., spring or others). The wedge can also be activated, pushed or pulled, by a shaft, through a percutaneous procedure or by an implantable mechanism such as an electric motor, magnet arrangement or other means known to those skilled in the art.

In one embodiment of the present invention, the spinal cage may include a ratchet mechanism. After implanting the spinal cage, and after the patient has recovered from the operation, the patient is encouraged to bend to the corrective direction. The rotatable mechanism captures any minor incremental angular correction and then allows the patient's body to get used to the new position. This way, step by step in small increments, the deformity can be corrected.

BRIEF DESCRIPTION OF DRAWINGS

The present invention will be understood and appreciated more fully from the following detailed description, taken in conjunction with the drawings in which.

DETAILED DESCRIPTION OF EMBODIMENTS

Figure 1:
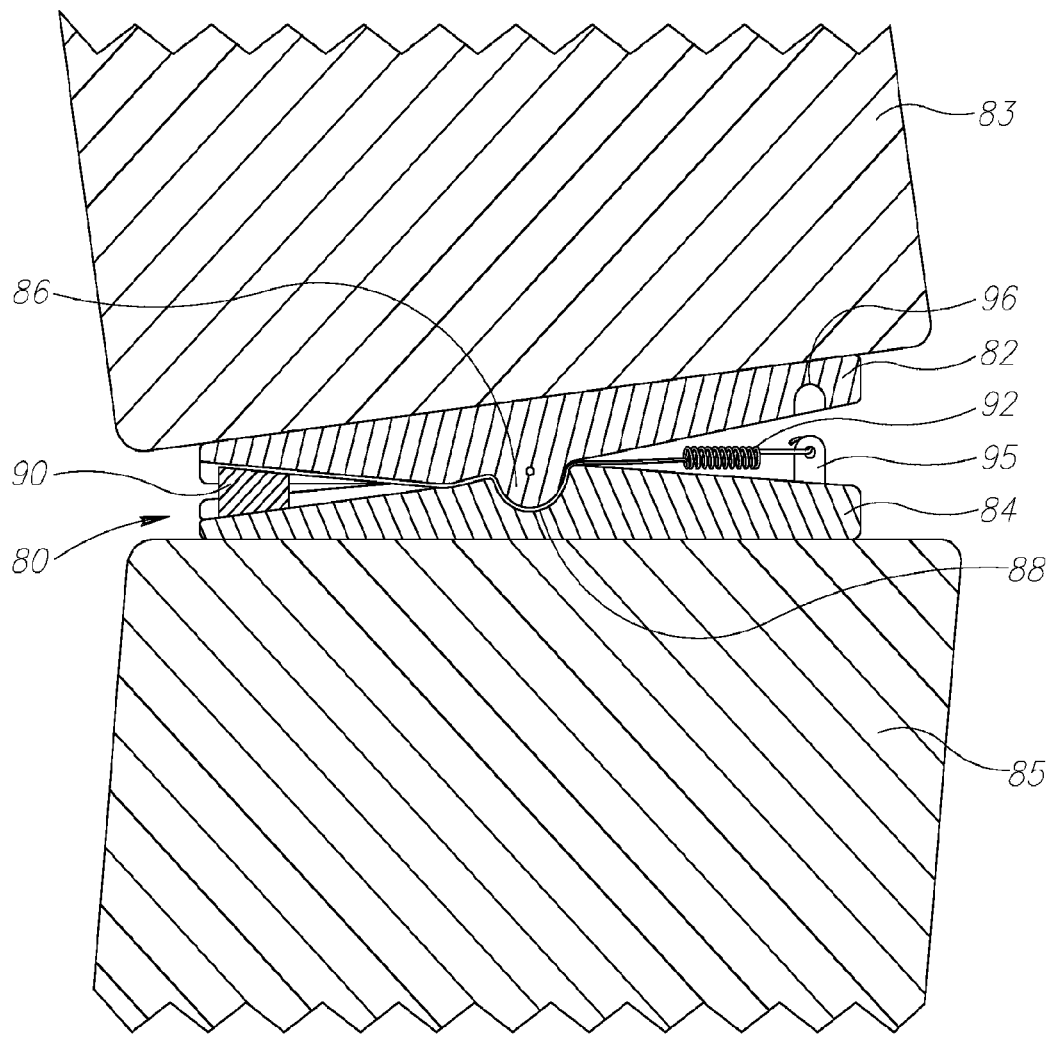
FIG. 1 is a simplified pictorial illustration of a longitudinal cross section of a uni-directional rotatable spinal cage, constructed and operative in accordance with a non-limiting embodiment of the present invention.

Reference is now made to FIG. 1, which illustrates a rotatable spinal cage 80, constructed and operative in accordance with an embodiment of the invention.

Spinal cage 80 includes first and second spinal attachment members 82 and 84, which may be, without limitation, flat plates. First and second spinal attachment members 82 and 84 are attached to two adjacent vertebrae 83 and 85, respectively. The plates may have coarse or roughened surfaces that interface with the vertebrae for enhanced binding to the vertebra bone or tissue (other adhesion enhancers may be used as well, such as coatings for binding with tissue and the like). For example, fixation of spinal cage 80 can be enhanced by means of spikes, screws or other means known to those skilled in the art.

First and second spinal attachment members 82 and 84 articulate with one another by means of an articulation joint. Accordingly, spinal cage 80 can pivot about the articulation joint in one rotational degree of freedom. In the illustrated embodiment, the articulation joint includes a male member 86 which is pivotally received in a female member 88. In the illustrated embodiment, the male member 86 extends from first spinal attachment member 82 and the female member 88 is formed in second spinal attachment member 84. Of course, the reverse can also be made.

A wedge element 90 is arranged for wedging between first and second spinal attachment members 82 and 84. Wedge element 90 may have a generally conical or trapezoidal shape or any other shape that can be accommodated by first and second spinal attachment members 82 and 84. An actuator 92 is linked to wedge element 90 for moving wedge element 90 in a direction that wedges wedge element 90 further in between members 82 and 84 (i.e., increases the wedging effect) or further away from members 82 and 84 (i.e., decreases the wedging effect). Actuator 92 can be, without limitation, a spring, motor, linear actuator, solenoid and the like. Actuator 92 can pull or push wedge element 90 directly or through a string, rod or any other connecting element.

The surfaces of first and second spinal attachment members 82 and 84 that contact wedge element 90 can be polished, roughened, grooved, etc., to increase the friction between the wedge and the members. In one embodiment, wedge element 90 can have a threaded hole, pin, groove and the like, for grasping with a tool to enable pulling the wedge and to release the uni-directional mechanism and allow some rotation of the attachment members 82 and 84 to another direction.

Figure 2:
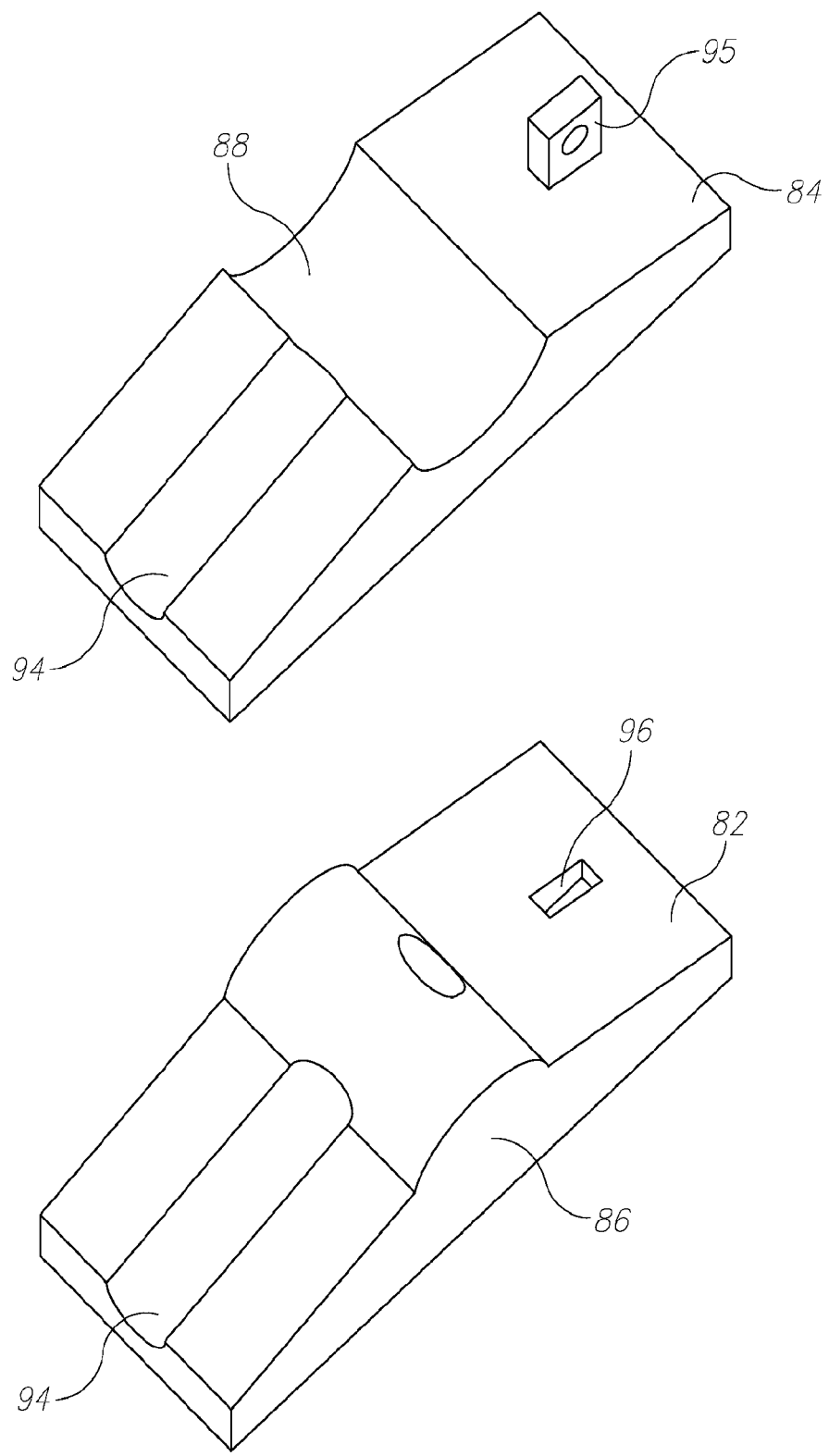
FIG. 2 is a simplified pictorial illustration of first and second spinal attachment members of the spinal cage of FIG. 1, in accordance with an embodiment of the present invention.

Referring now to FIG. 2, it is seen that first and second spinal attachment members 82 and 84 may be formed with grooves 94 for accommodating therein wedge element 90 (not shown in FIG. 2). A stopper 95 which is received in a depression 96 may be provided on first and second spinal attachment members 82 and 84. Actuator 92 may be attached to stopper 95, as seen in FIG. 1. Stopper may be used to limit the pivoting motion of spinal cage 80.

Figure 3:
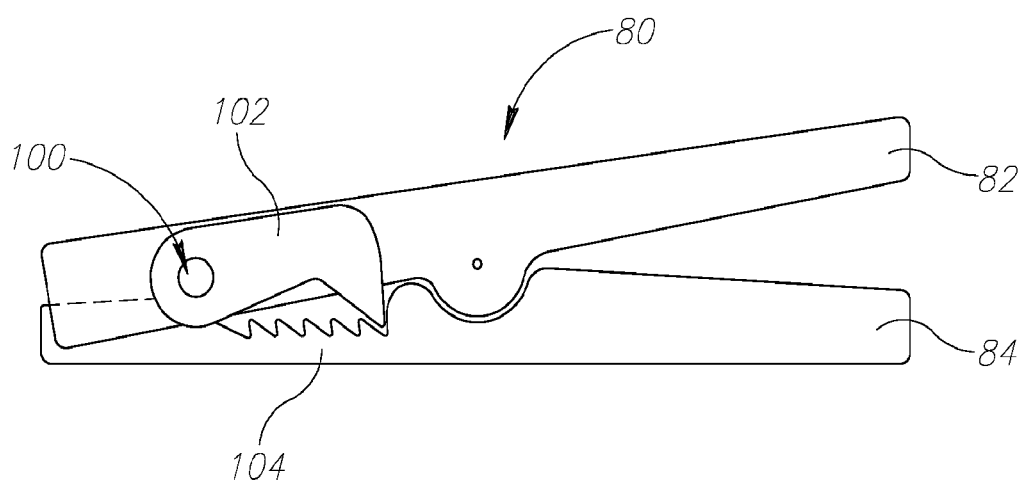
FIG. 3 is a simplified pictorial illustration of the uni-directional rotatable spinal cage, constructed and operative in accordance with another embodiment of the invention, and including a ratchet mechanism.

Reference is now made to FIG. 3, which illustrates another version rotatable spinal cage 80, constructed and operative in accordance with an embodiment of the invention. In this embodiment, a ratchet mechanism 100, including a pawl 102 and tooth rack 104 are mounted on first and second spinal attachment members 82 and 84. In this manner, spinal cage 80 may be rotated and locked in any desired rotational orientation.

What is claimed is:

1. A spinal cage comprising: first and second spinal attachment members attachable to vertebrae, said first and second spinal attachment members articulating with one another by means of an articulation joint; and a wedge element arranged for wedging between said first and second spinal attachment members, and an actuator comprising a spring which is linked to said wedge element for moving said wedge element in a direction that wedges said wedge element further in between said first and second spinal attachment members or further away from said first and second spinal attachment members, wherein said articulation joint comprises a male member which is pivotally received in a female member.

2. The spinal cage according to claim 1, wherein said first and second spinal attachment members are formed with grooves for accommodating therein said wedge element.

3. The spinal cage according to claim 1, wherein said articulation joint permits articulation thereabout in one rotational degree of freedom.

4. The spinal cage according to claim 1, wherein said first and second spinal attachment members comprise flat plates.

5. The spinal cage according to claim 1, wherein a stopper is received in a depression provided on said first and second spinal attachment members.

6. The spinal cage according to claim 1, wherein said wedge element and said spring are positioned on opposite sides of said articulation joint.

7. The spinal cage according to claim 5, wherein said wedge element and said stopper are positioned on opposite sides of said articulation joint.

\* \* \* \* \*